(12) United States Patent
Kim et al.

(10) Patent No.: US 8,437,849 B2
(45) Date of Patent: May 7, 2013

(54) METHOD AND APPARATUS FOR ATRIAL PACING DURING TACHYARRHYTHMIA

(75) Inventors: Jaeho Kim, Redmond, WA (US); Joseph M. Bocek, Seattle, WA (US); Dan Li, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 922 days.

(21) Appl. No.: 11/668,627

(22) Filed: Jan. 30, 2007

(65) Prior Publication Data

US 2008/0183228 A1 Jul. 31, 2008

(51) Int. Cl.
*A61N 1/372* (2006.01)
*A61N 1/39* (2006.01)

(52) U.S. Cl.
USPC .................................... 607/14; 607/9; 607/4

(58) Field of Classification Search .................. 607/5, 4, 607/9, 14
See application file for complete search history.

(56) References Cited

U.S. PATENT DOCUMENTS

| | | | |
|---|---|---|---|
| 4,998,974 A | 3/1991 | Aker | |
| 6,658,286 B2 | 12/2003 | Seim | |
| 6,708,058 B2 | 3/2004 | Kim et al. | |
| 6,915,161 B2 | 7/2005 | Kim | |
| 7,162,300 B2 | 1/2007 | van Groeningen et al. | |
| 2004/0172067 A1 | 9/2004 | Saba | |
| 2004/0220624 A1 | 11/2004 | Ritscher et al. | |
| 2005/0070966 A1 | 3/2005 | Sharma | |
| 2005/0149125 A1* | 7/2005 | Kim et al. | ............... 607/5 |
| 2006/0217769 A1 | 9/2006 | Saba | |
| 2007/0135848 A1 | 6/2007 | Kim et al. | |
| 2007/0142866 A1 | 6/2007 | Li | |
| 2007/0173894 A1 | 7/2007 | Li | |
| 2007/0191894 A1 | 8/2007 | Li | |
| 2007/0197928 A1 | 8/2007 | Kim et al. | |
| 2007/0260283 A1 | 11/2007 | Li | |
| 2007/0282381 A1 | 12/2007 | Li | |
| 2009/0099616 A1 | 4/2009 | Li et al. | |

OTHER PUBLICATIONS

Saba, S., et al., "New method for real-time discrimination and management of ventricular and supraventricular tachyarrhythmias applicable to patients with dual-chamber cardioverter-defibrillators", *Am J Cardiol.*, 93(1), (2004), 111-4.

Saba, S., et al., "Simultaneous atrial and ventricular anti-tachycardia pacing as a novel method of rhythym discrimination.", *J Cardiovasc Electrophysiol.*, 17(7), (2006), 695-701.

* cited by examiner

*Primary Examiner* — Joseph Stoklosa
(74) *Attorney, Agent, or Firm* — Schwegman Lundberg & Woessner, P.A.

(57) ABSTRACT

An implantable cardioverter/defibrillator (ICD) delivers atrial pacing under several scenarios during a tachyarrhythmia episode that is detected using a ventricular rate. In various embodiments, the atrial pacing terminates the detected tachyarrhythmia and/or enhances the classification of the detected tachyarrhythmia, thus avoiding ineffective and/or unnecessary delivery of a ventricular anti-tachyarrhythmia therapy when the detected tachyarrhythmia has a supraventricular origin.

28 Claims, 7 Drawing Sheets

METHOD AND APPARATUS FOR ATRIAL PACING DURING TACHYARRHYTHMIA

TECHNICAL FIELD

This document relates generally to cardiac rhythm management (CRM) systems and particularly to a system providing for atrial pacing during tachyarrhythmia with a fast ventricular rate to avoid ineffective and/or unnecessary delivery of ventricular anti-tachyarrhythmia therapy whenever possible.

BACKGROUND

Tachyarrhythmias are abnormal heart rhythms characterized by a rapid heart rate. Tachyarrhythmia generally includes supraventricular tachyarrhythmia and ventricular tachyarrhythmia. Fibrillation is a form of tachyarrhythmia further characterized by an irregular heart rhythm. In a normal heart, the sinoatrial (SA) node, the heart's predominant natural pacemaker, generates electrical impulses, called action potentials, that propagate through an electrical conduction system to the atria and then to the ventricles of the heart to excite the myocardial tissues. The atria and ventricles contract in the normal atrio-ventricular sequence and synchrony to result in efficient blood-pumping functions indicated by a normal hemodynamic performance. Ventricular tachyarrhythmia occurs when the electrical impulses propagate along a pathologically formed self-sustaining conductive loop within the ventricles or when a biologic pacemaker (focus) in a ventricle usurps control of the heart rate from the SA node. When the atria and the ventricles become dissociated during ventricular tachyarrhythmia, the ventricles may contract before they are properly filled with blood, resulting in diminished blood flow throughout the body. This condition becomes life-threatening when the brain is deprived of sufficient oxygen supply. Ventricular fibrillation (VF), in particular, stops blood flow within seconds and, if not timely and effectively treated, causes immediate death. In very few instances a heart recovers from VF without treatment.

Ventricular cardioversion and defibrillation are used to terminate most ventricular tachyarrhythmias, including ventricular tachycardia (VT), and VF. An implantable cardioverter/defibrillator (ICD) is a cardiac rhythm management (CRM) device that delivers cardioversion/defibrillation pulses, each being an electric shock, to terminate a detected tachyarrhythmia episode by depolarizing the entire myocardium simultaneously and rendering it refractory.

Another type of electrical therapy for tachyarrhythmia is anti-tachycardia pacing (ATP), including atrial ATP for treating atrial tachyarrhythmia and ventricular ATP for treating ventricular tachyarrhythmia. In ATP, the heart is competitively paced in an effort to interrupt the reentrant loop causing the tachyarrhythmia. In an ICD that includes ATP and cardioversion/defibrillation capabilities, the efficacy of each available anti-tachyarrhythmia therapy depends on the type and origin of the tachyarrhythmia. For example, a ventricular anti-tachycardia pacing therapy is generally ineffective in terminating an atrial tachyarrhythmia. Additionally, the delivery of each cardioversion/defibrillation pulse consumes a considerable amount of power and results in patient discomfort owing to the high voltage of the shock pulses. If delivered during the atrial vulnerable period, a cardioversion/defibrillation pulse may also cause atrial fibrillation. Therefore, for therapy efficacy, device longevity, and patient satisfaction, among other reasons, there is a need for an ICD to avoid ineffective and/or unnecessary delivery of ventricular anti-tachyarrhythmia therapy whenever possible.

SUMMARY

An ICD delivers atrial pacing under several scenarios during a tachyarrhythmia episode that is detected using a ventricular rate. In various embodiments, the atrial pacing is applied to terminate the detected tachyarrhythmia and/or to enhance the classification of the detected tachyarrhythmia, thus avoiding ineffective and/or unnecessary delivery of a ventricular anti-tachyarrhythmia therapy when the detected tachyarrhythmia has a supraventricular origin.

In one embodiment, an ICD includes a pacing circuit, a defibrillation circuit, a rate detector, a tachyarrhythmia detection and classification circuit, and a pacing controller. The pacing circuit delivers atrial and ventricular pacing pulses. The defibrillation circuit delivers ventricular defibrillation pulses. The cardiac sensing circuit senses cardiac signals. The rate detector detects an atrial rate and a ventricular rate using the cardiac signals. The tachyarrhythmia detection and classification circuit includes a tachyarrhythmia detector and a tachyarrhythmia classifier. The tachyarrhythmia detector detects tachyarrhythmia using the ventricular rate and one or more tachyarrhythmia threshold rates. The tachyarrhythmia classifier classifies the detected tachyarrhythmia. The pacing controller controls the delivery of the atrial and ventricular pacing pulses and includes an atrial pacing initiator. The atrial pacing initiator initiates the delivery of the atrial pacing pulses in a selected atrial pacing mode during the detected tachyarrhythmia if the detected tachyarrhythmia is classified as a ventricular tachyarrhythmia while one or more indications for atrial tachyarrhythmia are detected.

In one embodiment, an method of operating an ICD is provided. Cardiac signals are sensed. An atrial rate and a ventricular rate are detected using the cardiac signals. Tachyarrhythmia is detected using the ventricular rate and one or more tachyarrhythmia threshold rates. The detected tachyarrhythmia is classified. If the detected tachyarrhythmia is classified as a ventricular tachyarrhythmia and one or more indications for atrial tachyarrhythmia are detected, a delivery of atrial pacing pulses in a selected atrial pacing mode is initiated.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
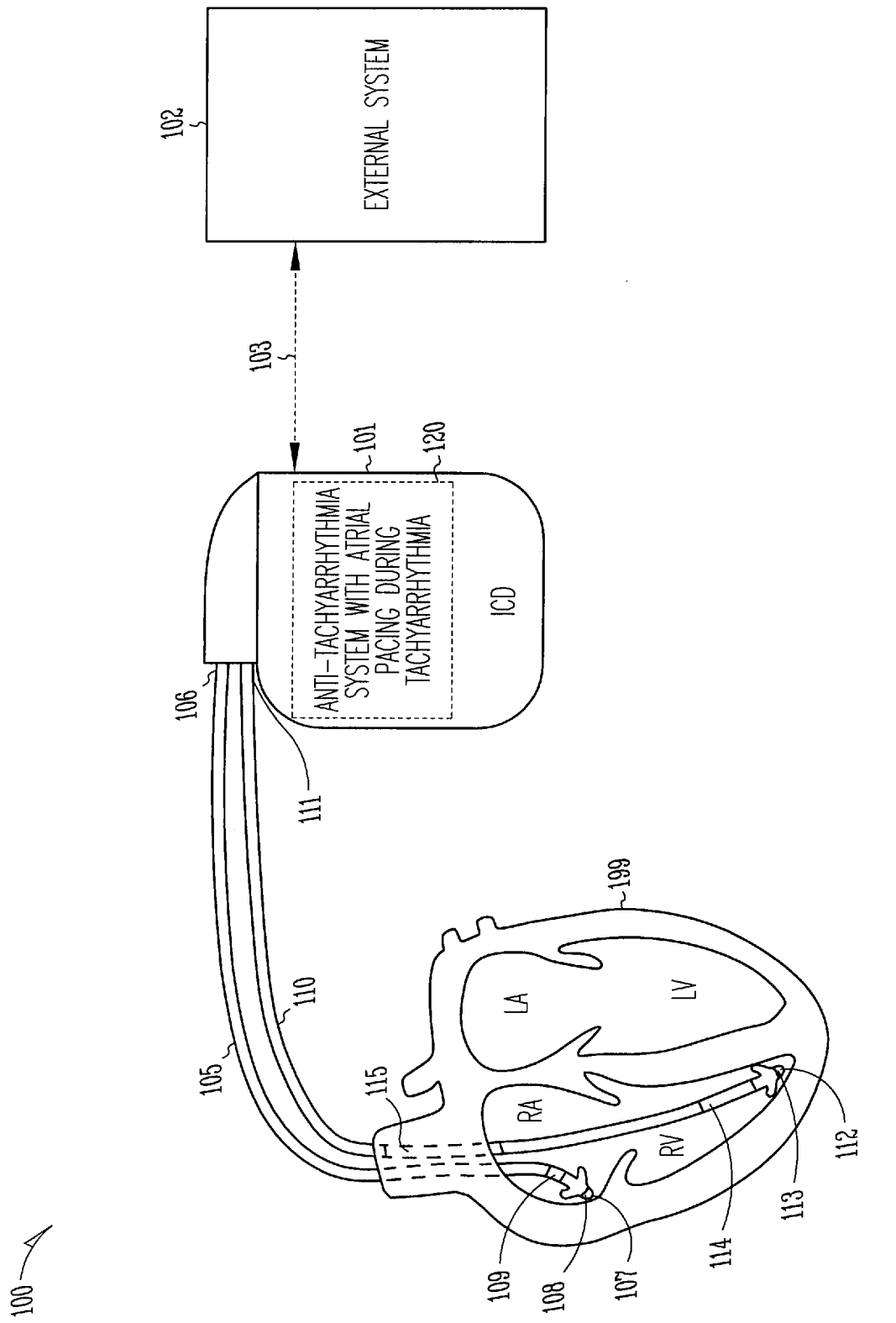
FIG. 1 is an illustration of an embodiment of a CRM system and portions of the environment in which the CRM system operates.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description provides examples, and the scope of the present invention is defined by the appended claims and their legal equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

It should be noted that references to "an", "one", or "various" embodiments in this document are not necessarily to the same embodiment, and such references contemplate more than one embodiment.

The relationship between a heart rate and a cardiac cycle length (also known as cardiac interval), as used in this document, is the relationship between a frequency and its corresponding period. If a heart rate is given in beats per minute (bpm), its corresponding cardiac cycle length in milliseconds is calculated by dividing 60,000 by the heart rate (where 60,000 is the number of milliseconds in a minute). Any process, such as a comparison, using a heart rate is to be modified accordingly when a cardiac cycle length is used instead. For example, if a tachyarrhythmia is detected when the ventricular rate exceeds a tachyarrhythmia threshold rate, an equivalent process is to detect the tachyarrhythmia when the ventricular cycle length (also known as ventricular interval) falls below a tachyarrhythmia threshold interval. The appended claims should be construed to cover such variations.

In this document, a "fast beat" refers to a heart beat having a heart rate that falls into a tachyarrhythmia detection zone, which is typically defined by at least one tachyarrhythmia detection threshold, and a "slow beat" refers to a heart beat having a heart rate that is below the tachyarrhythmia detection zone. In other words, a "fast beat" is a heart beat having a tachyarrhythmic heart rate, and a "slow beat" is a heart beat having a heart rate that is not tachyarrhythmic.

This document discusses, among other things, an ICD that delivers atrial pacing prior to delivering ventricular anti-tachyarrhythmia therapy if atrial arrhythmia is indicated after a tachyarrhythmia is detected when a ventricular electrogram indicates a fast ventricular rate. A tachyarrhythmia is detected, for example, when the ventricular rate falls within a predetermined tachyarrhythmia rate zone defined by one or more tachyarrhythmia detection thresholds. During and/or following the detection, the tachyarrhythmia is classified to determine the necessity and type of a therapy. Because ventricular tachyarrhythmia can be fatal without immediate treatment, the classification process helps ensure that a necessary ventricular therapy is not inappropriately delayed or withheld. On the other hand, because a ventricular therapy such as ventricular defibrillation causes significant pain in the patient and shortens the life expectancy of the ICD, it is also desirable to avoid ineffective and/or unnecessary delivery of the ventricular therapy. For example, it has been observed that after a tachyarrhythmia is detected based on the ventricular rate and classified as an atrial tachyarrhythmia such as atrial fibrillation (AF) or atrial flutter (AFL), rhythm and waveform characteristics known to be associated with VT may be temporarily present in the ventricular electrogram, leading to an inaccurate VT classification. A subsequent ventricular therapy would be neither necessary nor effective in treating the atrial tachyarrhythmia. The present implantable CRM device delivers atrial pacing after a tachyarrhythmia is detected to avoid such unnecessary, ineffective, and painful ventricular therapy if one or more indications for an atrial tachyarrhythmia are present. In various embodiments discussed in this document, the atrial pacing is delivered to terminate an atrial tachyarrhythmia and/or to enhance the classification of the tachyarrhythmia, thereby reducing or preventing inaccurate VT classification and hence, ineffective and/or unnecessary delivery of the ventricular therapy.

FIG. 1 is an illustration of an embodiment of a CRM system 100 and portions of the environment in which CRM system 100 operates. CRM system 100 includes an ICD 101 that is electrically coupled to a heart 199 through leads 105 and 110. An external system 102 communicates with ICD 101 via a telemetry link 103.

ICD 101 includes a hermetically sealed can housing an electronic circuit that senses physiological signals and delivers therapeutic electrical pulses. The hermetically sealed can may also function as an electrode for sensing and/or pulse delivery purposes. In one embodiment, as illustrated in FIG. 1, the electronic circuit senses at least an atrial electrogram and a ventricular electrogram from heart 199 and delivers pacing and cardioversion/defibrillation pulses to heart 199. Lead 105 is typically a pacing lead that includes a proximal end 106 connected to ICD 101 and a distal end 107 placed in the right atrium (RA) of heart 199. A pacing-sensing electrode 108 is located at distal end 107. Another pacing-sensing electrode 109 is located near distal end 107. Electrodes 108 and 109 are electronically connected to ICD 101 via separate conductors in lead 105 to allow for sensing of the atrial electrogram and/or delivery of atrial pacing pulses. Lead 110 is typically a defibrillation lead that includes a proximal end 111 connected to ICD 101 and a distal end 112 placed in the right ventricle (RV) of heart 199. A pacing-sensing electrode 113 is located at distal end 112. A defibrillation electrode 114 is located near distal end 112 but electrically separated from pacing-sensing electrode 113. Another defibrillation electrode 115 is located at a distance from distal end 112 for supraventricular placement. Electrodes 113, 114, and 115 are electrically connected to ICD 101 via separate conductors in lead 110. Electrode 113 and 114 allow for sensing of the ventricular electrogram and/or delivery of ventricular pacing pulses. Electrodes 114 and 115 allow for delivery of ventricular cardioversion/defibrillation pulses. The functions of these electrodes are discussed above by way of example and not by way of limitation. Other ways of using these electrodes are possible as understood by those of skill in the art.

ICD 101 includes an anti-tachyarrhythmia system providing for atrial pacing, including atrial ATP, during tachyarrhythmia with a fast ventricular rate or a fast atrial rate while the ventricular rate is slow. In one embodiment, the anti-tachyarrhythmia system delivers anti-tachyarrhythmia therapies including atrial ATP, ventricular ATP, and ventricular cardioversion/defibrillation pulses, according to the classification of each detected tachyarrhythmia. In one embodiment, an atrial ATP therapy is delivered if a detected tachyarrhythmia is classified as an atrial tachyarrhythmia. If the detected tachyarrhythmia is classified as a ventricular tachyarrhythmia, but one or more indications for an atrial tachyarrhythmia are present, an atrial ATP therapy is delivered prior to the delivery of ventricular ATP and/or ventricular cardioversion/defibrillation therapies. In another embodiment, atrial pacing pulses are delivered to enhance the classification of the tachyarrhythmia, thereby helping prevent inaccurate VT classification and hence, ineffective and/or unnecessary delivery of the ventricular therapy. Embodiments of structure and operation of various elements of ICD 101 are discussed below with reference to FIGS. 2-7.

External system 102 allows for programming of ICD 101 and receives signals acquired by ICD 101. In one embodiment, external system 102 includes a programmer. In another embodiment, external system 102 is a patient management system including an external device in proximity of ICD 101, a remote device in a relatively distant location, and a telecommunication network linking the external device and the remote device. The patient management system provides for access to ICD 101 from a remote location, such as for monitoring patient status and/or adjusting therapies. In one embodiment, telemetry link 103 is an inductive telemetry link. In an alternative embodiment, telemetry link 103 is a far-field radio-frequency telemetry link. Telemetry link 103 provides for data transmission from ICD 101 to external system 102. This may include, for example, transmitting real-time physiological data acquired by ICD 101, extracting physiological data acquired by and stored in ICD 101, extracting therapy history data stored in ICD 101, and extracting data indicating an operational status of ICD 101 (e.g., battery status and lead impedance). Telemetry link 103 also provides for data transmission from external system 102 to ICD 101. This may include, for example, programming ICD 101 to acquire physiological data, programming ICD 101 to perform at least one self-diagnostic test (such as for a device operational status), programming ICD 101 to run a signal analysis algorithm (such as an algorithm implementing a tachyarrhythmia classification method discussed in this document), and programming ICD 101 to deliver pacing and/or cardioversion/defibrillation therapies.

The circuit of ICD 101, including its various elements discussed in this document, may be implemented using a combination of hardware and software. In various embodiments, each element of ICD 101 discussed in this document may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof. For example, a "comparator" includes, among other things, an electronic circuit comparator constructed to perform the only function of a comparison between two signals or a portion of a general-purpose circuit driven by a code instructing that portion of the general-purpose circuit to perform the comparison between the two signals.

Figure 2:
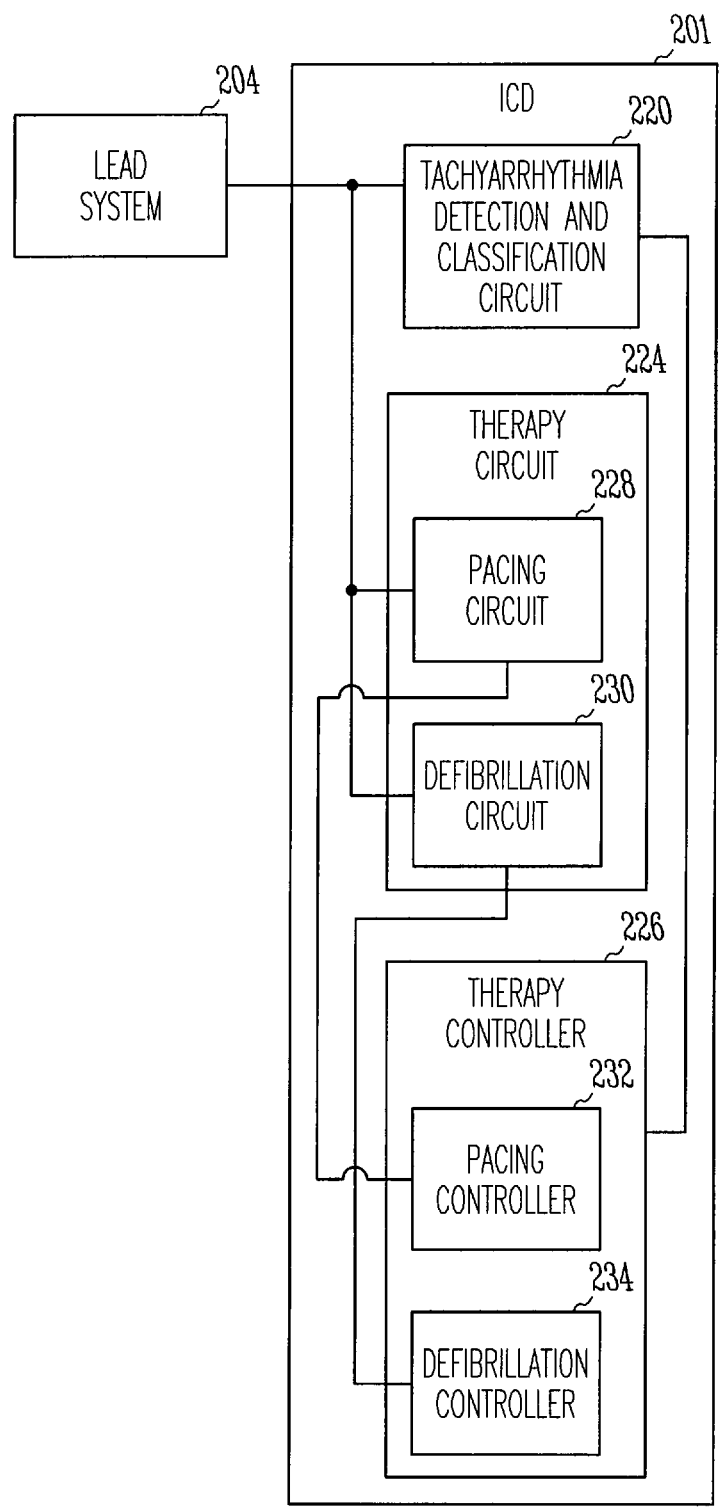
FIG. 2 is a block diagram illustrating an embodiment of an ICD and a lead system of the CRM system.

FIG. 2 is a block diagram illustrating an embodiment of an ICD 201 and a lead system 204. Lead system 204 includes one or more leads such as leads 105 and 110. ICD 201 is a specific embodiment of ICD 101 and includes a tachyarrhythmia detection and classification circuit 220, a therapy circuit 224, and a therapy controller 226. Tachyarrhythmia detection and classification circuit 220 detects and classifies tachyarrhythmia episode using at least one or more intrinsic electrical cardiac signals sensed using lead system 204. In one embodiment, in addition to one or more cardiac signals, tachyarrhythmia detection and classification circuit 220 uses one or more other physiological signals, such as one or more signals indicative of hemodynamic performance, to detect and classify tachyarrhythmia episode. Therapy circuit 224 includes a pacing circuit 228 to deliver pacing pulses to heart 199 through lead system 204 and a defibrillation circuit 230 to deliver cardioversion/defibrillation pulses to heart 199 through lead system 204. Therapy controller 226 includes a pacing controller 232 to control the delivery of the pacing pulses and a defibrillation controller 234 to control the delivery of the cardioversion/defibrillation pulses. Therapy controller 226 selects one or more of pacing and cardioversion/defibrillation therapies based on the classification of the tachyarrhythmia episode. In one embodiment, a ventricular ATP therapy is delivered if a detected tachyarrhythmia is classified as a type of ventricular tachyarrhythmia known to be treatable by the ventricular ATP therapy. If the ventricular ATP therapy fails to terminate the tachyarrhythmia, a ventricular cardioversion/defibrillation therapy is delivered. In one embodiment, an atrial ATP therapy is delivered prior to delivering a ventricular anti-tachyarrhythmia therapy if a detected tachyarrhythmia is classified as a ventricular tachyarrhythmia, but one or more indications for atrial tachyarrhythmia are present. In a specific embodiment, the atrial ATP is delivered during the preparation for delivering a ventricular defibrillation pulse, and requires little or no delay in delivering the ventricular defibrillation therapy. If the detected tachyarrhythmia is terminated by the atrial ATP therapy, the delivery of the ventricular defibrillation therapy is canceled. In another embodiment, the atrial ATP is delivered while ventricular anti-tachyarrhythmia therapy is inhibited.

Figure 3:
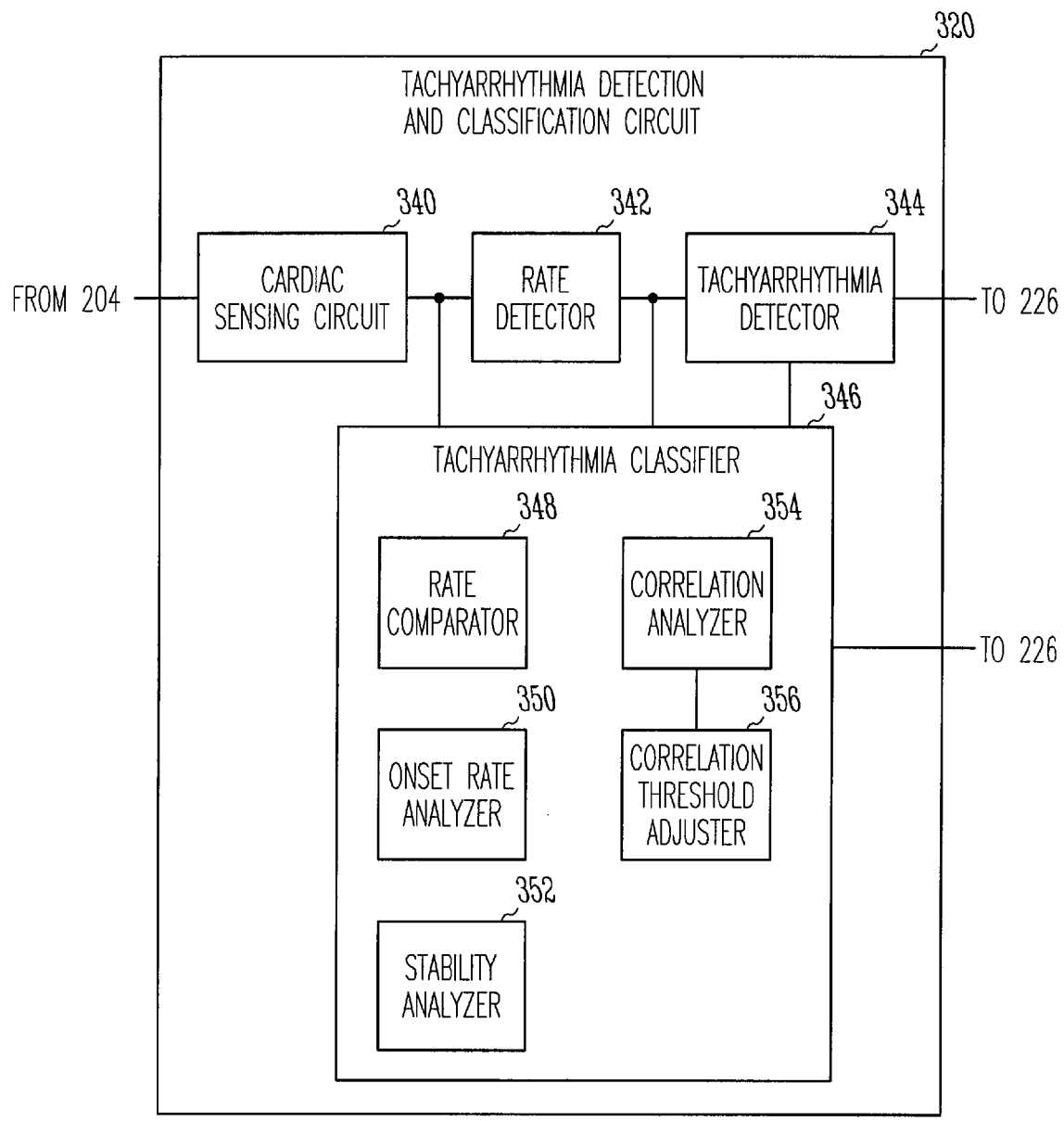
FIG. 3 is a block diagram illustrating an embodiment of a tachyarrhythmia detection and classification circuit of the ICD.

FIG. 3 is a block diagram illustrating an embodiment of a tachyarrhythmia detection and classification circuit 320. Tachyarrhythmia detection and classification circuit 320 is a specific embodiment of tachyarrhythmia detection and classification circuit 220 and includes a cardiac sensing circuit 340, a rate detector 342, a tachyarrhythmia detector 344, and a tachyarrhythmia classifier 346.

Cardiac sensing circuit 340 senses one or more cardiac signals, such as one or more electrograms, through lead system 204. In one embodiment, cardiac sensing circuit 340 is electrically coupled to heart 199 through lead system 204 to sense an atrial electrogram and a ventricular electrogram from the heart. The atrial electrogram includes atrial events, also known as P waves, each indicative of an atrial depolarization. The ventricular electrogram includes ventricular events, also known as R waves, each indicative of a ventricular depolarization.

Rate detector 342 detects one or more heart rates from one or more cardiac signals sensed by cardiac sensing circuit 340. In one embodiment, rate detector 342 detects an atrial rate from the atrial electrogram and a ventricular rate from the ventricular electrogram. The atrial rate is the frequency of the atrial events. The ventricular rate is the frequency of the ventricular events. In one embodiment, the atrial and ventricular rates are each expressed in beats per minute (bpm), i.e., number of detected atrial or ventricular depolarizations per minute.

Tachyarrhythmia detector 344 detects a tachyarrhythmia episode. In one embodiment, a tachyarrhythmia is detected when the ventricular rate exceeds a predetermined tachyarrhythmia threshold rate. In one embodiment, tachyarrhythmia detector 344 detects tachyarrhythmia by determining whether the ventricular rate is within one of a plurality of tachyarrhythmia rate zones each including a predetermined threshold rate. In a specific embodiment, the plurality of tachyarrhythmia rate zones includes a VF rate zone with a VF threshold rate programmable between 130 and 250 bpm, a fast VT rate zone with a fast VT threshold rate programmable between 110 and 210 bpm, and a slow VT rate zone with a slow VT threshold rate programmable between 90 and 200 bpm. In another embodiment, the tachyarrhythmia is detected using a "zoneless tachyarrhythmia detection" method, as discussed in U.S. patent application Ser. No. 11/301,716, "ZONELESS TACHYARRHYTHMIA DETECTION WITH REAL-TIME RHYTHM MONITORING", filed on Dec. 13, 2005, assigned to Cardiac Pacemakers, Inc., which is incorporated herein by reference in its entirety.

Tachyarrhythmia classifier 346 classifies each tachyarrhythmia detected by tachyarrhythmia detector 344. Examples of classification of tachyarrhythmia made by tachyarrhythmia classifier 346 include ventricular fibrillation (VF), ventricular tachycardia (VT), supraventricular tachyarrhythmia (SVT), atrial fibrillation (AF), atrial flutter (AFL), sinus tachycardia (ST), and atrial tachycardia (AT). In one embodiment, a detected tachyarrhythmia is classified as VF when the ventricular rate falls within the VF rate zone, without further analysis by tachyarrhythmia classifier 346. In the illustrated embodiment, tachyarrhythmia classifier 346 includes a rate comparator 348, an onset rate analyzer 350, a stability analyzer 352, a correlation analyzer 354, and a correlation threshold adjuster 356. Rate comparator 348 compares the atrial rate and the ventricular rate to determine whether the atrial rate exceeds, equals, or is lower than the ventricular rate by a predetermined margin. Onset rate analyzer 350 produces an onset rate of the detected tachyarrhythmia and determines whether the detected tachyarrhythmia has a gradual onset or a sudden onset by comparing the onset rate to one or more threshold onset rates. The onset rate is a rate of transition of the ventricular rate from a normal sinus rate to a tachyarrhythmic rate when the detected tachyarrhythmia begins. A gradual onset typically indicates a physiological tachyarrhythmia, such as an ST caused by exercise. A sudden onset typically indicates a pathological tachyarrhythmia. Stability analyzer 352 produces a stability parameter indicative of a degree of ventricular rate variability and determines whether the ventricular rate is stable by comparing the stability parameter to a stability threshold. In one embodiment, the stability parameter is produced as an average variance of a series of ventricular intervals. Correlation analyzer 354 analyzes a correlation between a tachyarrhythmic waveform and a template waveform and produces a correlation coefficient representative of that correlation. The tachyarrhythmic waveform includes a segment of a cardiac signal sensed during the detected tachyarrhythmia. The template waveform is recorded during a known cardiac rhythm such as the normal sinus rhythm (NSR). One example for producing such a correlation coefficient, referred to as a feature correlation coefficient (FCC), is discussed in U.S. Pat. No. 6,708,058, "NORMAL CARDIAC RHYTHM TEMPLATE GENERATION SYSTEM AND METHOD," assigned to Cardiac Pacemakers, Inc., which is hereby incorporated in its entirety. In one embodiment, the detected tachyarrhythmia is considered as "correlated" if a correlation coefficient exceeds a correlation threshold and as "marginally correlated" if the correlation coefficient exceeds a marginal correlation threshold that is lower than the correlation threshold. Correlation threshold adjuster 356 allows adjustment of the marginal correlation threshold. Tachyarrhythmia classifier 346 classifies the detected tachyarrhythmia using one or more of the atrial rate, ventricular rate, onset rate, stability parameter, and correlation coefficient.

In one embodiment, tachyarrhythmia classifier 346 classifies the detected tachyarrhythmia using a method discussed below with reference to FIG. 4. In addition, tachyarrhythmia classifier 346 detects one or more indications specified for one or more types of tachyarrhythmia. If the one or more indications specified for a predetermined type tachyarrhythmia are detected, tachyarrhythmia classifier 346 indicates that predetermined type tachyarrhythmia. The one or more indications include characteristics of the one or more cardiac signals that suggest a possibility or likeliness that the detected tachyarrhythmia is of a certain type, but are not sufficient to classify the detected tachyarrhythmia as that certain type using specified classification criteria. Examples of such characteristics include the atrial rate, ventricular rate, onset rate, stability parameter, and correlation coefficient used by tachyarrhythmia classifier 346. Based on such characteristics, tachyarrhythmia classifier 346 may classify the detected tachyarrhythmia as one type of tachyarrhythmia while indicating a possibility of another type of tachyarrhythmia. While the classification of the detected tachyarrhythmia as one type of tachyarrhythmia ensures that a necessary therapy is not withheld or inappropriately delayed, the indications for a different type of tachyarrhythmia allows an unnecessary therapy to be withheld or canceled. For example, a detected tachyarrhythmia may be classified as VT using specified classification criteria, but if one or more indications for AF or AFL are detected (i.e., AF or AFL is indicated), an atrial ATP therapy may be delivered prior to the delivery of a ventricular anti-tachyarrhythmia therapy. If the atrial ATP fails to terminate the detected tachyarrhythmia because it is indeed VT, the ventricular anti-tachyarrhythmia therapy is delivered. If the atrial ATP successfully terminates the detected tachyarrhythmia because it is indeed AF or AFL, the ventricular anti-tachyarrhythmia therapy is canceled. Thus, the delivery of an unnecessary and/or ineffective ventricular anti-tachyarrhythmia therapy may be avoided without compromising patient safety.

In one embodiment, tachyarrhythmia detector 344 performs a detection process that is initiated by a detection of three consecutive fast beats from the ventricular electrogram. In response to the detection of three consecutive fast beats, a tachyarrhythmia detection window is started. The tachyarrhythmia detection window includes ten consecutively detected heart beats starting with and including the three consecutive fast beats. If at least eight out of the ten heart beats in the tachyarrhythmia detection window are fast beats (i.e., the tachyarrhythmia detection window is satisfied), a tachyarrhythmia verification duration is started. Otherwise, the tachyarrhythmia verification duration is not started.

During the tachyarrhythmia verification duration, a moving verification window of ten consecutively detected heart beats is used to determine whether the detected tachyarrhythmia sustains. If at least six out of the ten heart beats in the verification window are fast beats (i.e., the verification window is satisfied), the detected tachyarrhythmia is considered to be sustaining. If this verification window fails to be satisfied at any time during the tachyarrhythmia verification duration, the tachyarrhythmia detection is terminated without delivering an anti-tachyarrhythmia therapy. If the detected tachyarrhythmia episode is determined to be sustaining throughout the tachyarrhythmia verification duration, it is classified by tachyarrhythmia classifier 346 to determine the necessity and type of an anti-tachyarrhythmia therapy.

If the detected tachyarrhythmia is classified as a type of tachyarrhythmia for which a ventricular cardioversion/defibrillation therapy is to be delivered, such as a VT episode, the preparation for the delivery of the ventricular cardioversion/defibrillation shock pulse is started. In one embodiment, if the detected tachyarrhythmia is classified as VT, but one or more indications for AF or AFL are detected, an atrial ATP therapy is delivered during the preparation for the delivery of the ventricular cardioversion/defibrillation shock pulse. After the preparation for the delivery of the ventricular cardioversion/defibrillation shock pulse is completed, a tachyarrhythmia reconfirmation window of three consecutive heart beats is started, immediately before a scheduled ventricular cardioversion/defibrillation pulse delivery. If at least two out of the three heart beats in the tachyarrhythmia reconfirmation window are fast beats (i.e., the tachyarrhythmia reconfirmation window is satisfied), the detected tachyarrhythmia is considered to be still sustaining, and the ventricular cardioversion/defibrillation pulse is delivered. On the other hand, if the detected tachyarrhythmia is classified as a type of tachyarrhythmia for which a ventricular anti-tachycardia pacing therapy is to be delivered, ventricular anti-tachycardia pacing pulses are delivered without starting the reconfirmation window for checking whether the detected tachyarrhythmia sustains.

If the detected tachyarrhythmia episode is classified as a type of tachyarrhythmia for which no ventricular anti-tachyarrhythmia therapy is needed, such as an SVT episode, a sustained rate duration (SRD) time window may be started, depending on whether it is programmed to be applied. During the SRD, the ventricular rate is monitored to determine whether the tachyarrhythmia episode sustains. If the tachyarrhythmia episode sustains throughout the SRD, the ventricular anti-tachyarrhythmia therapy is delivered when the SRD expires even though the detected tachyarrhythmia episode is classified as an SVT episode. The tachyarrhythmia episode sustains if the ventricular rate remains within the fast or slow VT rate zone. In one embodiment, the tachyarrhythmia episode is considered sustaining when an average ventricular rate (such as an average of ventricular rates detected within a moving window) falls within the fast or slow VT rate zone. In another embodiment, the tachyarrhythmia episode is considered sustaining when a predetermined majority of ventricular beats within a moving detection window are fast beats, such as when at least six out of ten heart beats are fast beats. In one embodiment, if the SRD is programmed to be applied ("ON"), its value is programmable between 10 seconds and 60 minutes, with approximately three minutes as a specific example. The SRD is applied to determine whether a detected tachyarrhythmia needs to be treated because of a sustaining high ventricular rate, after the tachyarrhythmia is classified to be a type that is not to be treated. Thus, the SRD functions as a "safety net" capable of overriding a tachyarrhythmia classification to deliver a therapy. During the SRD, tachyarrhythmia classifier 346 continues to classify the detected tachyarrhythmia and update the classification when necessary. If, for example, the classification changes from SVT to VT during the SRD, a ventricular anti-tachyarrhythmia is to be delivered.

Figure 4:
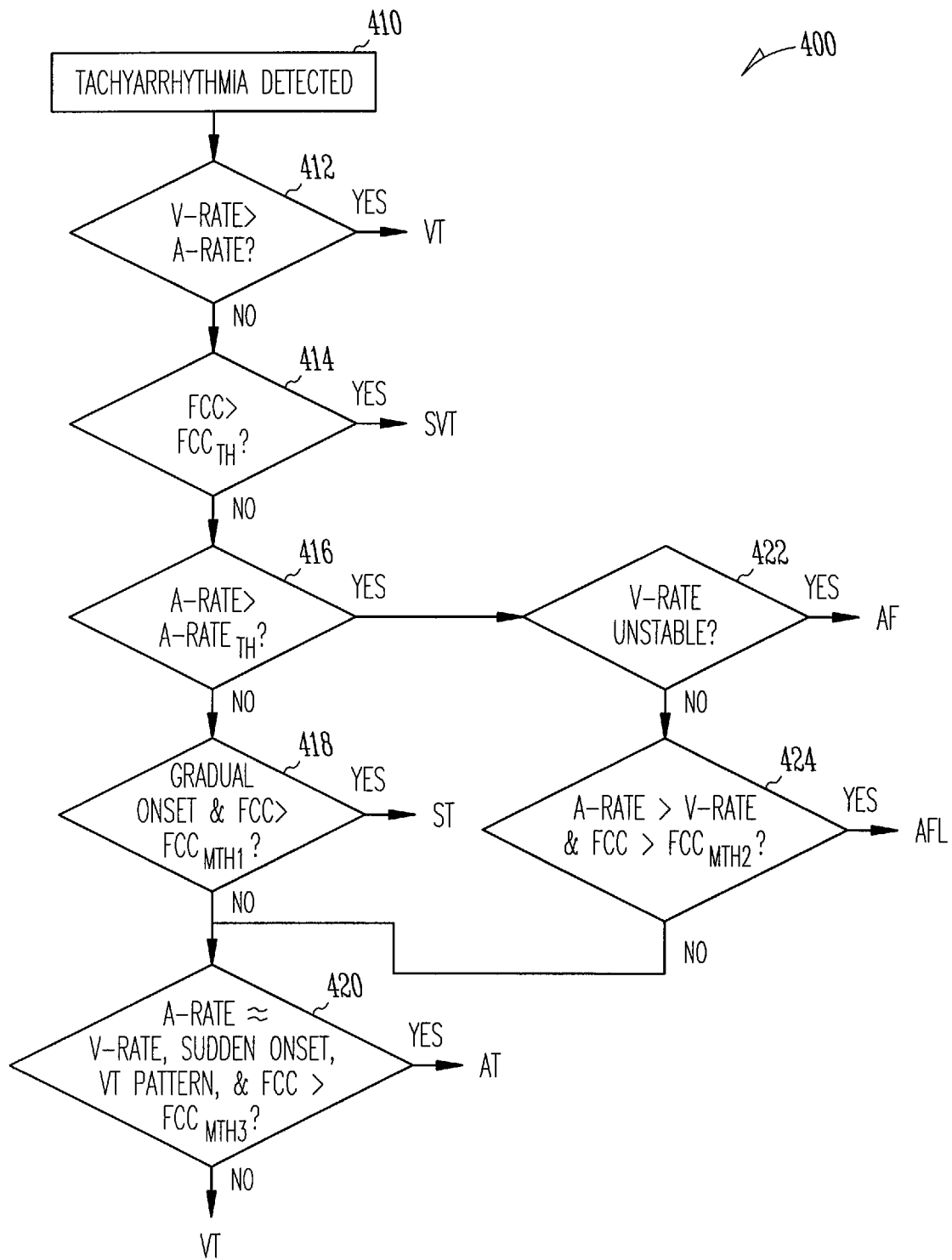
FIG. 4 is a flow chart illustrating a method for classifying detected tachyarrhythmia.

FIG. 4 is a flow chart illustrating a method 400 for classifying a detected tachyarrhythmia. In one embodiment, tachyarrhythmia classifier 346 performs method 400. The atrial rate, ventricular rate, onset rate, stability parameter, correlation coefficient, and various thresholds used in method 400 are detected, produced, or programmed as discussed with reference to FIG. 3 above. For correlation analysis, the template waveform is produced using a cardiac signal sensed during an NSR.

A tachyarrhythmia is detected at 410, when the ventricular rate is within a predetermined tachyarrhythmia rate zone. If the ventricular rate (V-RATE) exceeds the atrial rate (A-RATE) by a predetermined margin at 412, the detected tachyarrhythmia is classified as VT. If the ventricular rate does not exceed the atrial rate by a predetermined margin at 412, and the correlation coefficient (FCC) exceeds the correlation threshold ($FCC_{TH}$) at 414, the detected tachyarrhythmia is classified as SVT. In one embodiment, the correlation threshold ($FCC_{TH}$) is programmable between 0.6 and 0.99, with approximately 0.94 being a specific example.

If the atrial rate does not exceed a predetermined threshold atrial rate (A-$RATE_{TH}$) at 416, the onset rate indicates a gradual onset of tachyarrhythmia at 418, and the correlation coefficient exceeds a first marginal correlation threshold ($FCC_{MTH1}$) (i.e., FCC falls between $FCC_{MTH1}$ and $FCC_{TH}$) at 418, the detected tachyarrhythmia is classified as ST. ST is a physiologic tachyarrhythmia originated in an SA node when the SA node generates the electrical impulses at a tachyarrhythmic rate. In one embodiment, the first marginal correlation coefficient is programmable between 0.4 and the correlation threshold (i.e., $0.4 \leq FCC_{MTH1} \leq FCC_{TH}$), with approximately 0.8 being a specific example. In one embodiment, the first marginal correlation threshold is set to be lower than the correlation threshold by a predetermined amount, such as approximately 0.2 (i.e., $FCC_{MTH1} \approx FCC_{TH} - 0.2$).

If the correlation coefficient does not exceed the correlation threshold at 414, the atrial rate exceeds a predetermined threshold atrial rate at 416, and the ventricular rate is unstable at 422, the detected tachyarrhythmia is classified as AF. If the ventricular rate is stable at 422, the atrial rate exceeds the ventricular rate by a predetermined margin, and the correlation coefficient exceeds a second marginal correlation threshold ($FCC_{MTH2}$) (i.e., FCC falls between $FCC_{MTH2}$ and $FCC_{TH}$) at 424, the detected tachyarrhythmia is classified as AFL. In one embodiment, the second marginal correlation threshold is programmable between 0.4 and the correlation threshold (i.e., $0.4 \leq FCC_{MTH2} \leq FCC_{TH}$), with approximately 0.8 being a specific example. In one embodiment, the second marginal correlation threshold is set to be lower than the correlation threshold by a predetermined amount, such as approximately 0.2 (i.e., $FCC_{MTH2} \approx FCC_{TH} - 0.2$).

If the atrial rate approximately equals to the ventricular rate at 420, the onset rate indicates a sudden onset of tachyarrhythmia, the atrial and ventricular events occur in a specified SVT pattern, and the correlation coefficient exceeds a third marginal correlation threshold ($FCC_{MTH3}$) (i.e., FCC falls between $FCC_{MTH3}$ and $FCC_{TH}$) at 420, the detected tachyarrhythmia is classified as AT. The detection of cardiac event patterns including the SVT pattern is discussed in U.S. patent application Ser. No. 11/276,213, entitled "RHYTHM DISCRIMINATION OF SUDDEN ONSET AND ONE-TO-ONE TACHYARRHYTHMIA", filed on Feb. 17, 2006, assigned to Cardiac Pacemakers, Inc., which is hereby incorporated in its entirety. If these conditions are not met at 420, the detected tachyarrhythmia is classified as VT. AT is a pathologic tachyarrhythmia that occurs when a biologic pacemaker (focus) in an atrium usurps control of the heart rate from the SA node. In one embodiment, the third marginal correlation threshold ($FCC_{MTH3}$) is programmable between 0.4 and the correlation threshold (i.e., $0.4 \leq FCC_{MTH3} \leq FCC_{TH}$), with approximately 0.6 being a specific example. In one embodiment, the third marginal correlation threshold is set to be lower than the correlation threshold by a predetermined amount, such as approximately 0.4 (i.e., $FCC_{MTH3} \approx FCC_{TH} - 0.2$).

Figure 5:
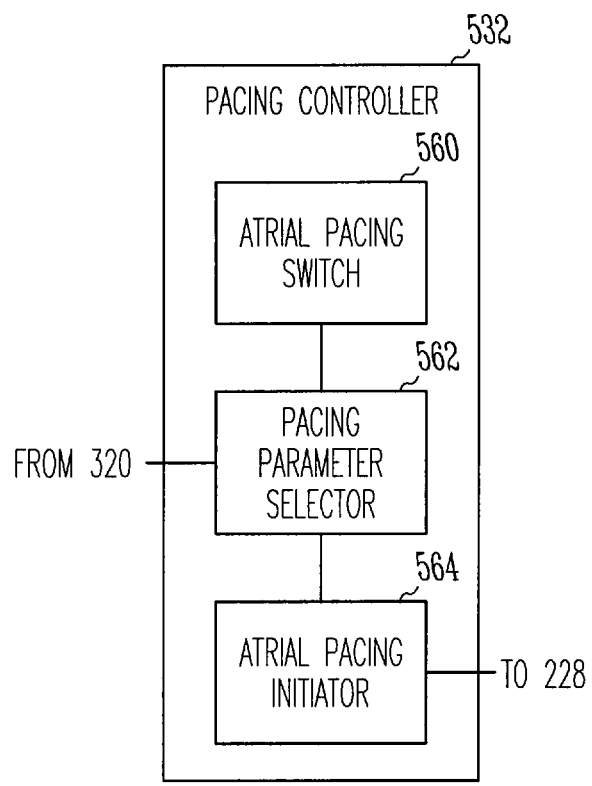
FIG. 5 is a block diagram illustrating an embodiment of a circuit of a pacing controller of the ICD.

FIG. 5 is a block diagram illustrating an embodiment of a circuit of a pacing controller 532. Pacing controller 532 is a specific embodiment of pacing controller 232 and includes an atrial pacing switch 560, a pacing parameter selector 562, and an atrial pacing initiator 564.

Atrial pacing switch 560 allows for enabling and disabling of atrial pacing during the tachyarrhythmia detected using the ventricular rate. In response to an atrial pacing activation command, atrial pacing switch 560 enables atrial pacing while the tachyarrhythmia is detected. In response to an atrial pacing deactivation command, atrial pacing switch 560 inhibits atrial pacing while the tachyarrhythmia is detected. In one embodiment, the atrial pacing activation command and the atrial pacing deactivation command are entered by a user such as a physician or other caregiver using external system 102 and telemetered to ICD 101 via telemetry link 103. In another embodiment, the atrial pacing activation command and/or the atrial pacing deactivation command are generated within ICD 101 using one or more programmed automatic detection criteria. For example, the atrial pacing deactivation command may be automatically generated in response to a detection of a condition of the patient that suggests ineffectiveness of atrial pacing in terminating a detected tachyarrhythmia and/or necessity of immediate ventricular anti-tachyarrhythmia therapy.

Pacing parameter selector 562 selects one or more pacing parameters including the pacing mode. In one embodiment, pacing parameter selector 562 is programmed to select an atrial ATP mode for atrial pacing during the detected tachyarrhythmia. In a specific embodiment, pacing parameter selector 562 further selects one or more pacing parameters for controlling the delivery of atrial pacing pulses in the atrial ATP mode. Examples of such pacing parameters include number of bursts of pacing pulses to be delivered in each ATP therapy, number of pacing pulses in each burst, coupling interval, and pacing rate. In one embodiment, pacing parameter selector 562 selects the one or more pacing parameters using the classification of detected tachyarrhythmia. In another embodiment, pacing parameter selector 562 is programmed to select a bradycardia pacing mode, such as the AAI or AOO mode, and a pacing rate that is higher than the detected intrinsic atrial rate.

Atrial pacing initiator 564 initiates the delivery of the atrial pacing pulses in the selected pacing mode if the detected tachyarrhythmia is classified as an atrial tachyarrhythmia such as AF or AFL, or the delivery of the atrial pacing pulses in the selected pacing mode prior to delivering a ventricular anti-tachyarrhythmia therapy if the detected tachyarrhythmia is classified as VT but one or more indications for atrial tachyarrhythmia are detected. In one embodiment, the atrial pacing is delivered for purposes of restoring a sinus rhythm. In another embodiment, the atrial pacing is delivered for purposes of classifying the detected tachyarrhythmia. In one embodiment, atrial pacing initiator 564 reinitiates the delivery of atrial pacing pulses in the ATP mode for a limited number of attempts (such as two bursts of ATP pulses) if the detected tachyarrhythmia sustains and continues to be classified as AF or AFL and ventricular anti-tachyarrhythmia therapy is inhibited after the delivery of the atrial pacing pulses in the ATP mode.

In one embodiment, atrial pacing initiator 564 initiates the delivery of the atrial pacing pulses in an ATP mode if the ventricular rate is within the slow VT rate zone, the detected tachyarrhythmia is classified as VT using method 400, and one of AF and AFL is indicated. In one embodiment, one of AF and AFL is indicated if the atrial rate exceeds the ventricular rate and the correlation coefficient is between a lower marginal correlation threshold and the second marginal correlation threshold ($FCC_{LMTH}$) (i.e., FCC falls between $FCC_{LMTH}$ and $FCC_{MTH2}$). In one embodiment, the lower marginal correlation threshold is programmable between 0.4 and the second marginal correlation threshold (i.e., $0.4 \leq FCC_{LMTH} \leq FCC_{MTH2}$), with approximately 0.6 being a specific example. In one embodiment, the lower marginal correlation threshold is set to be lower than the second marginal correlation threshold by a predetermined amount, such as approximately 0.2 (i.e., $FCC_{LMTH} \approx FCC_{MTH2} - 0.2$). A atrial rate that is substantially higher than the ventricular rate, together with a correlation coefficient that exceeds the lower marginal correlation threshold, indicates that the detected tachyarrhythmia is possibly a supraventricular tachyarrhythmia treatable by the atrial ATP.

In another embodiment, atrial pacing initiator 564 initiates the delivery of the atrial pacing pulses at a pacing rate higher than the detected atrial rate if the ventricular rate is within the slow VT rate zone, the detected tachyarrhythmia is classified as VT, and ST is indicated. In one embodiment, ST is indicated if the correlation coefficient is between the lower marginal correlation threshold and the first marginal correlation threshold (i.e., FCC falls between $FCC_{LMTH}$ and $FCC_{MTH1}$), and the detected tachyarrhythmia has a gradual onset while the atrial and ventricular rates are approximately equal. In one embodiment, if ST is confirmed following the delivery of the atrial pacing pulses at the pacing rate higher than the detected atrial rate, correlation threshold adjuster 356 decreases the marginal correlation threshold ($FCC_{MTH1}$) for tachyarrhythmia classification using method 400 to the lower marginal correlation threshold ($FCC_{LMTH}$). ST is confirmed if the ventricular rate follows the pacing rate during the delivery of the atrial pacing pulses at the pacing rate higher than the detected atrial rate.

Figure 6:
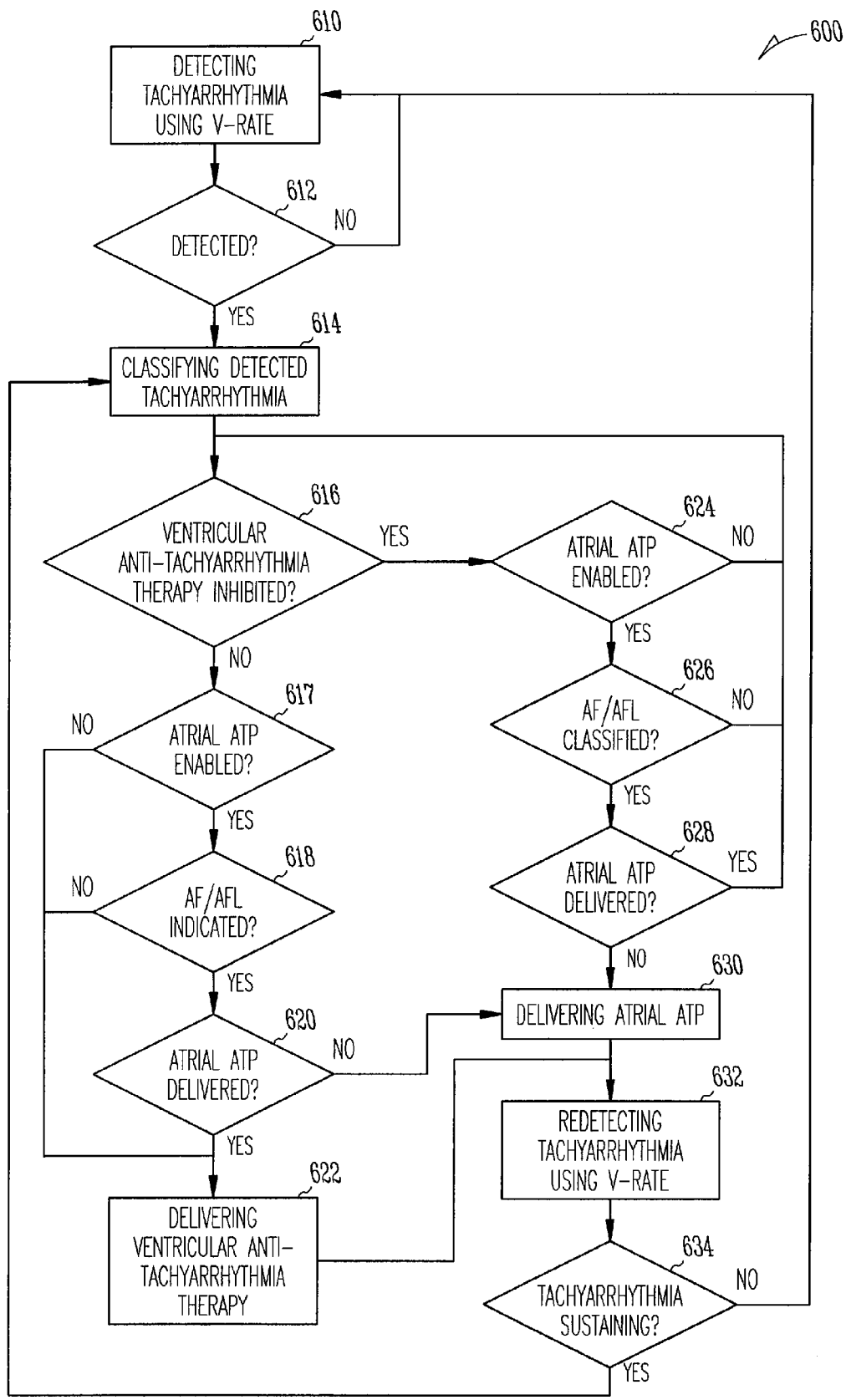
FIG. 6 is a flow chart illustrating an embodiment of a method for controlling atrial pacing during tachyarrhythmia.
Figure 7:
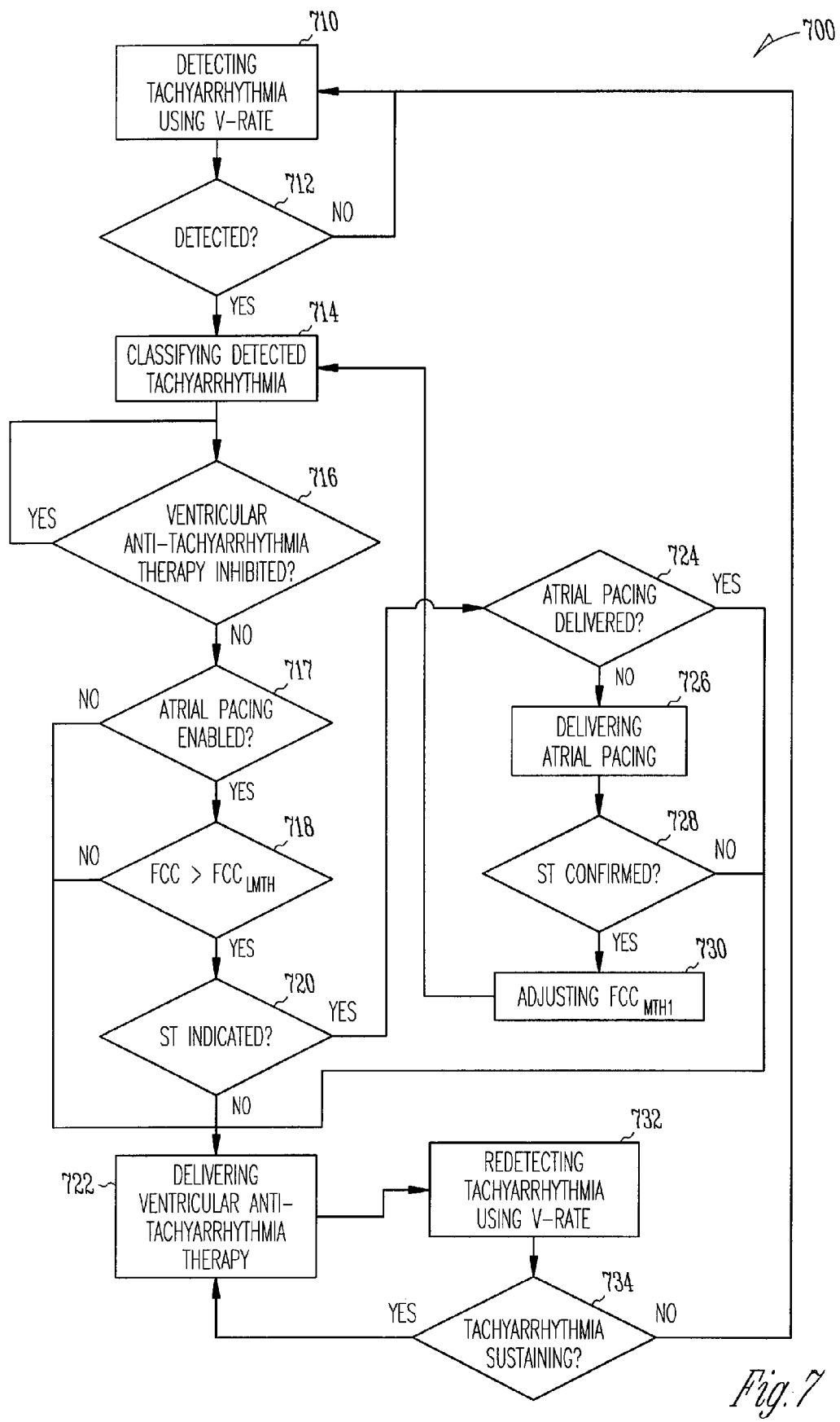
FIG. 7 is a flow chart illustrating another embodiment of a method for controlling atrial pacing during tachyarrhythmia.

FIGS. 6 and 7 illustrate methods 600 and 700 each being a specific example of applying atrial pacing during a tachyarrhythmia detected based on the fast ventricular rate. These specific examples are discussed below for illustrative, but not restrictive, purposes. In various embodiments, pacing controller 532 is programmed to perform one or more of methods 600 and 700.

FIG. 6 is a flow chart illustrating an embodiment of method 600 for controlling atrial pacing during tachyarrhythmia. Method 600 is performed as an attempt to terminate the detected tachyarrhythmia.

Tachyarrhythmia is being detected using the ventricular rate at 610. If a tachyarrhythmia is detected at 612, the detected tachyarrhythmia is classified at 614. In one embodiment, the detected tachyarrhythmia is classified at 614 using method 400 as discussed above. If the detected tachyarrhythmia is classified as VT using method 400, ventricular anti-tachyarrhythmia therapy (such as ventricular ATP and/or ventricular cardioversion/defibrillation therapy) is not inhibited. If the detected tachyarrhythmia is classified as one of ST, SVT, AT, AF, and AFL using method 400, the ventricular anti-tachyarrhythmia therapy is inhibited.

If the detected tachyarrhythmia is classified as one for which the ventricular anti-tachyarrhythmia therapy (such as ventricular ATP and/or ventricular cardioversion/defibrillation therapy) is not inhibited at 616, atrial ATP is enabled for delivery during a tachyarrhythmia detected based on the fast ventricular rate at 617, and one or more indications for AF or AFL are detected at 618, whether atrial ATP therapy has been used in attempt to terminate the detected tachyarrhythmia is determined at 620. An example for indicating AF or AFL is discussed above with reference to FIG. 5. If the atrial ATP is not enabled at 617, no indication for AF or AFL is detected at 618, or the atrial ATP therapy has been delivered (or a specified maximum number of atrial ATP bursts has been reached) during the detected tachyarrhythmia at 620, the ventricular anti-tachyarrhythmia therapy is delivered at 622. If the one or more indications for AF or AFL are detected at 618, and the atrial ATP therapy has not been delivered (or the specified maximum number of atrial ATP bursts has not been reached) during the detected tachyarrhythmia at 620, the atrial ATP therapy is delivered at 630. In one embodiment, the preparation for delivering the ventricular anti-tachyarrhythmia therapy starts when the detected tachyarrhythmia is classified as one for which the ventricular anti-tachyarrhythmia therapy is not inhibited at 616, though the actual delivery may be canceled, for example, after the atrial ATP therapy successfully terminates the detected tachyarrhythmia.

If the detected tachyarrhythmia is classified as one for which the ventricular anti-tachyarrhythmia therapy is inhibited at 616, whether to deliver atrial pacing is to be determined. If atrial pacing is enabled for delivery during a tachyarrhythmia detected based on the fast ventricular rate at 624, the detected arrhythmia is classified as AF or AFL at 626, and a specified maximum number of atrial ATP therapy deliveries for the detected tachyarrhythmia episode (such as two) has not been reached at 628, the atrial ATP therapy is delivered at 630.

Following the delivery of the ventricular anti-tachyarrhythmia therapy at 622 or the delivery of the atrial ATP therapy at 630, the tachyarrhythmia is being redetected using the ventricular rate at 632 to determine whether the tachyarrhythmia sustains or has been terminated. If the tachyarrhythmia sustains at 634, it is re-classified at 614, and the ventricular anti-tachyarrhythmia therapy are repeatedly delivered as necessary until the tachyarrhythmia is terminated or the programmed therapies are exhausted.

FIG. 7 is a flow chart illustrating an embodiment of method 700 for controlling atrial pacing during tachyarrhythmia. Method 700 is performed for purposes of classifying a detected tachyarrhythmia by modifying the classification criteria based on the heart's response to the atrial pacing during tachyarrhythmia.

Tachyarrhythmia is being detected using the ventricular rate at 710. If a tachyarrhythmia is detected at 712, the detected tachyarrhythmia is classified at 714. In one embodiment, the detected tachyarrhythmia is classified at 714 using method 400 as discussed above. If the detected tachyarrhythmia is classified as VT using method 400, ventricular anti-tachyarrhythmia therapy (such as ventricular ATP and/or ventricular cardioversion/defibrillation therapy) is not inhibited. If the detected tachyarrhythmia is classified as one of ST, SVT, AT, AF, and AFL using method 400, the ventricular anti-tachyarrhythmia therapy is inhibited.

If the detected tachyarrhythmia is classified as one for which a ventricular anti-tachyarrhythmia therapy (such as ventricular ATP and/or ventricular cardioversion/defibrillation therapy) is not inhibited at 716, atrial pacing is not enabled for delivery during a tachyarrhythmia detected based on the fast ventricular rate at 717, or the correlation coefficient does not exceeds a specified lower marginal correlation threshold ($FCC_{LMTH}$) at 718, the ventricular anti-tachyarrhythmia therapy is delivered at 722. If the detected tachyarrhythmia is classified as one for which the ventricular anti-tachyarrhythmia therapy is not inhibited at 716, the atrial ATP is enabled at 717, and the correlation coefficient exceeds the lower marginal correlation threshold at 718, but no indication for ST is detected at 720, the ventricular anti-tachyarrhythmia therapy is also delivered at 722. An example for indicating ST is discussed above with reference to FIG. 5. Following the delivery of the ventricular anti-tachyarrhythmia therapy, the tachyarrhythmia is being redetected using the ventricular rate at 732 to determine whether the tachyarrhythmia sustains or has been terminated. If the tachyarrhythmia sustains at 734, it is re-classified at 714, and the ventricular anti-tachyarrhythmia therapy is repeatedly delivered as necessary until the tachyarrhythmia is terminated or the programmed therapies are exhausted.

If the detected tachyarrhythmia is classified as one for which the ventricular anti-tachyarrhythmia therapy is not inhibited at 716, the atrial ATP is enabled at 717, the correlation coefficient exceeds the lower marginal correlation threshold at 718, and one or more indications for ST are present at 720, whether to deliver atrial pacing is to be determined. If the atrial pacing has not been delivered during the detected tachyarrhythmia at 724, the atrial pacing therapy is delivered at 726, using a pacing rate that is higher than the detected intrinsic rate. During the delivery of the atrial pacing, ST is being confirmed. ST is confirmed if the ventricular rate follows the pacing rate during the delivery of the atrial pacing pulses at the pacing rate higher than the detected atrial rate. If ST is confirmed at 728, a marginal correlation threshold used in the classification of the detected tachyarrhythmia (such as the first marginal correlation threshold, $FCC_{MTH1}$, in method 400) is lowered at 730 to allow a wider margin for a ST classification.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. An implantable cardioverter/defibrillator (ICD), comprising:
    a pacing circuit configured to deliver atrial and ventricular pacing pulses;
    a defibrillation circuit configured to deliver ventricular defibrillation pulses;
    a cardiac sensing circuit configured to sense cardiac signals;
    a rate detector configured to detect an atrial rate and a ventricular rate using the cardiac signals;
    a tachyarrhythmia detection and classification circuit coupled to the rate detector, the tachyarrhythmia detection and classification circuit including:
        a tachyarrhythmia detector configured to detect tachyarrhythmia using the ventricular rate and one or more tachyarrhythmia threshold rates; and
        a tachyarrhythmia classifier configured to classify the detected tachyarrhythmia as a ventricular tachyarrhythmia using one or more criteria including the ventricular rate being greater than the atrial rate and detect one or more indications for an atrial tachyarrhythmia; and a controller, coupled to the pacing circuit, the defibrillation circuit, and the tachyarrhythmia detection and classification circuit, the controller configured to control the delivery of the atrial and ventricular pacing pulses and the ventricular defibrillation pulses, the controller including:
an atrial pacing initiator configured to initiate the delivery of the atrial pacing pulses in a selected atrial pacing mode during the detected tachyarrhythmia and prior to a scheduled delivery of the ventricular pacing pulses or the ventricular defibrillation pulses in response to the detected tachyarrhythmia being classified as the ventricular tachyarrhythmia and one or more indications for the atrial tachyarrhythmia being detected; and
a ventricular pacing and defibrillation confirmation circuit configured to determine whether the scheduled delivery of the ventricular pacing pulses or the ventricular defibrillation pulses is to be initiated after the delivery of the atrial pacing pulses.

2. The ICD of claim 1, wherein the controller comprises an atrial pacing switch configured to enable the delivery of the atrial pacing pulses during the detected tachyarrhythmia in response to an atrial pacing activation command and to disable the delivery of the atrial pacing pulses during the detected tachyarrhythmia in response to an atrial pacing deactivation command.

3. The ICD of claim 2, wherein the controller comprises a pacing parameter selector configured to select one or more pacing parameters including a pacing mode using the detected one or more indications for the atrial tachyarrhythmia.

4. The ICD of claim 1, wherein the atrial pacing initiator is configured to initiate the delivery of the atrial pacing pulses in the selected atrial pacing mode in response to the ventricular rate being within a slow ventricular tachycardia (VT) rate zone below a predetermined fast VT threshold rate.

5. The ICD of claim 1, wherein the atrial pacing initiator is configured to initiate the delivery of the atrial pacing pulses in an atrial anti-tachycardia pacing (ATP) mode in response to the detected tachyarrhythmia being classified as the ventricular tachyarrhythmia and one or more indications for one of atrial fibrillation (AF) and atrial flutter (AFL) are detected.

6. The ICD of claim 5, wherein the atrial pacing initiator is configured to initiate the delivery of the atrial pacing pulses in the ATP mode in response to the atrial rate substantially exceeding the ventricular rate and a correlation coefficient being between a specified marginal correlation threshold and a specified lower marginal correlation threshold, the correlation coefficient representative of a correlation between a tachyarrhythmic waveform sensed during the detected tachyarrhythmia and a template waveform.

7. The ICD of claim 1, wherein the atrial pacing initiator is configured to initiate the delivery of the atrial pacing pulses at a pacing rate higher than the detected atrial rate in response to the detected tachyarrhythmia being classified as the ventricular tachyarrhythmia and one or more indications for sinus tachycardia (ST) being detected.

8. The ICD of claim 7, wherein the tachyarrhythmia classifier comprises a correlation analyzer configured to produce a correlation coefficient representative of a correlation between a tachyarrhythmic waveform and a template waveform and an onset rate analyzer configured to determine whether the detected tachyarrhythmia has a gradual onset indicative of physiological tachyarrhythmia or a sudden onset indicative of pathological tachyarrhythmia, and the atrial pacing initiator is configured to initiate the delivery of the atrial pacing pulses at a pacing rate higher than the detected atrial rate in response to the correlation coefficient being between a specified marginal correlation threshold and a specified lower marginal correlation threshold and the detected tachyarrhythmia having a gradual onset.

9. The ICD of claim 8, wherein the tachyarrhythmia classifier comprises a correlation threshold adjuster configured to decrease a marginal correlation threshold in response to ST being confirmed following the delivery of the atrial pacing pulses at the pacing rate higher than the detected atrial rate, the marginal correlation threshold used by the tachyarrhythmia classifier to classify the detected tachyarrhythmia.

10. The ICD of claim 9, wherein the tachyarrhythmia classifier is configured to confirm ST and configured to declare that ST is confirmed following the delivery of the atrial pacing pulses at the pacing rate higher than the detected atrial rate in response to the ventricular rate following the pacing rate during the delivery of atrial pacing pulses at the pacing rate higher than the detected atrial rate.

11. The ICD of claim 1, wherein the atrial pacing initiator is further configured to initiate the delivery of the atrial pacing pulses in an atrial anti-tachycardia pacing (ATP) mode in response to the detected tachyarrhythmia being classified as one of atrial fibrillation (AF) and atrial flutter (AFL).

12. A method of operating an implantable cardioverter/defibrillator (ICD), the method comprising:
sensing cardiac signals;
detecting an atrial rate and a ventricular rate using the cardiac signals;
detecting tachyarrhythmia using the ventricular rate and one or more tachyarrhythmia threshold rates;
classifying the detected tachyarrhythmia as a ventricular tachyarrhythmia using one or more criteria including the ventricular rate being greater than the atrial rate;
detecting one or more indications for an atrial tachyarrhythmia;
initiating a delivery of atrial pacing pulses in a selected atrial pacing mode during the detected tachyarrhythmia and prior to a scheduled delivery of ventricular pacing pulses or ventricular defibrillation pulses in response to the detected tachyarrhythmia being classified as the ventricular tachyarrhythmia and one or more indications for the atrial tachyarrhythmia are detected; and
determining whether to initiate the scheduled delivery of the ventricular pacing pulses or the ventricular defibrillation pulses after the delivery of the atrial pacing pulses.

13. The method of claim 12, comprising selecting one or more pacing parameters including the atrial pacing mode using the detected one or more indications for the atrial tachyarrhythmia.

14. The method of claim 13, comprising:
enabling atrial pacing while the tachyarrhythmia is detected in response to an atrial pacing activation command; and
disabling atrial pacing while the tachyarrhythmia is detected in response to an atrial pacing deactivation command.

15. The method of claim 14, comprising receiving the atrial pacing activation command and the atrial pacing deactivation command from a user using an external system communicatively coupled to the ICD via telemetry.

16. The method of claim 14, comprising generating one or more of the atrial pacing activation command and the atrial pacing deactivation command automatically using one or more programmed automatic detection criteria.

17. The method of claim 12, comprising suspending the detecting tachyarrhythmia during the delivery of the atrial pacing pulses in the selected atrial pacing mode.

18. The method of claim 12, wherein initiating the delivery of atrial pacing pulses in the selected atrial pacing mode comprises initiating the delivery of the atrial pacing pulses in the selected atrial pacing mode in response to the ventricular rate being within a slow ventricular tachycardia (VT) rate zone below a predetermined fast VT threshold rate.

19. The method of claim 12, wherein initiating the delivery of atrial pacing pulses in the selected atrial pacing mode comprises initiating the delivery of the atrial pacing pulses in an atrial anti-tachycardia pacing (ATP) mode in response to the detected tachyarrhythmia being classified as the ventricular tachyarrhythmia and one or more indications for one of atrial fibrillation (AF) and atrial flutter (AFL) being detected.

20. The method of claim 19, wherein initiating the delivery of atrial pacing pulses in the selected atrial pacing mode comprises initiating the delivery of the atrial pacing pulses in the ATP mode in response to the atrial rate substantially exceeding the ventricular rate and a correlation coefficient being between a specified marginal correlation threshold and a specified lower marginal correlation threshold, the correlation coefficient representative of a correlation between a tachyarrhythmic waveform sensed during the detected tachyarrhythmia and a template waveform.

21. The method of claim 12, wherein initiating the delivery of atrial pacing pulses in the selected atrial pacing mode comprises initiating the delivery of the atrial pacing pulses at a pacing rate higher than the atrial rate in response to the detected tachyarrhythmia being classified as the ventricular tachyarrhythmia and one or more indications for sinus tachycardia (ST) are detected.

22. The method of claim 21, further comprising:
producing a correlation coefficient representative of a correlation between a tachyarrhythmic waveform sensed during the detected tachyarrhythmia and a template waveform; and
determining whether the detected tachyarrhythmia has a gradual onset indicative of physiological tachyarrhythmia or a sudden onset indicative of pathological tachyarrhythmia,
and wherein initiating the delivery of the atrial pacing pulses at the pacing rate higher than the atrial rate comprises initiating the delivery of the atrial pacing pulses at the pacing rate higher than the atrial rate in response to the correlation coefficient being between a specified marginal correlation threshold and a specified lower marginal correlation threshold and the detected tachyarrhythmia has a gradual onset.

23. The method of claim 22, further comprising decreasing a marginal correlation threshold used in the classifying the detected tachyarrhythmia in response to ST being confirmed following the delivery of the atrial pacing pulses at the pacing rate higher than the detected atrial rate.

24. The method of claim 12, further comprising initiating the delivery of the atrial pacing pulses in an atrial anti-tachycardia pacing (ATP) mode in response to the detected tachyarrhythmia being classified as one of atrial fibrillation (AF) and atrial flutter (AFL).

25. The method of claim 12, comprising preparing for delivery of a cardioversion/defibrillation shock pulse and initiating the delivery of atrial pacing pulses in the selected atrial pacing mode during the preparation for the delivery of the cardioversion/defibrillation shock pulse in response to the detected tachyarrhythmia being classified as the ventricular tachyarrhythmia and the one or more indications for the atrial tachyarrhythmia are detected.

26. An implantable cardioverter/defibrillator (ICD), comprising:
means for sensing cardiac signals;
means for detecting an atrial rate and a ventricular rate using the cardiac signals;
means for detecting tachyarrhythmia using the ventricular rate and one or more tachyarrhythmia threshold rates;
means for classifying the detected tachyarrhythmia as a ventricular tachyarrhythmia using one or more criteria including the ventricular rate being greater than the atrial rate and detecting one or more indications for an atrial tachyarrhythmia;
means for initiating a delivery of atrial pacing pulses in a selected atrial pacing mode during the detected tachyarrhythmia and prior to a scheduled delivery of ventricular pacing pulses or ventricular defibrillation pulses in response to the detected tachyarrhythmia being classified as the ventricular tachyarrhythmia and one or more indications for the atrial tachyarrhythmia are detected; and
means for determining whether to initiate the scheduled delivery of the ventricular pacing pulses or the ventricular defibrillation pulses after the delivery of the atrial pacing pulses.

27. The ICD of claim 26, wherein the means for initiating the delivery of atrial pacing pulses comprises means for initiating a delivery of atrial pacing pulses in an atrial anti-tachycardia acing (ATP) mode in response to the detected tachyarrhythmia being classified as the ventricular tachyarrhythmia and one or more indications for one of atrial fibrillation (AF) and atrial flutter (AFL) are detected.

28. The ICD of claim 26, wherein the means for initiating the delivery of atrial pacing pulses comprises means for initiating the delivery of the atrial pacing pulses at a pacing rate higher than the atrial rate in response to the detected tachyarrhythmia being classified as the ventricular tachyarrhythmia and one or more indications for sinus tachycardia (ST) are detected.

* * * * *